(12) United States Patent
Yu et al.

(10) Patent No.: US 7,605,139 B2
(45) Date of Patent: Oct. 20, 2009

(54) DNA CANCER VACCINES

(75) Inventors: Dah-Shyong Yu, Taipei (TW);
Sun-Yran Chang, Taipei (TW);
Chi-Feng Lee, Taipei (TW)

(73) Assignee: National Defense Medical Center, Neihu, Taipei (TW)

( * ) Notice: Subject to any disclaimer, the term of this patent is extended or adjusted under 35 U.S.C. 154(b) by 604 days.

(21) Appl. No.: 11/064,672

(22) Filed: Feb. 24, 2005

(65) Prior Publication Data

US 2006/0189556 A1 Aug. 24, 2006

(51) Int. Cl.
*A61K 31/70* (2006.01)
(52) U.S. Cl. ...................................................... 514/44
(58) Field of Classification Search ................... 514/44
See application file for complete search history.

(56) References Cited

U.S. PATENT DOCUMENTS

| | | | | |
|---|---|---|---|---|
| 7,037,510 | B2 * | 5/2006 | Andersen et al. .......... | 424/248.1 |
| 2002/0176867 | A1 * | 11/2002 | Andersen et al. .......... | 424/190.1 |
| 2004/0057963 | A1 * | 3/2004 | Andersen et al. .......... | 424/190.1 |

OTHER PUBLICATIONS

Greenman et al, Nature 446:153-158, 2007.*
Goncalves, Bioessays. 27(5):506-517, 2005.*
Juengst, BMJ, 326:1410-11, 2003.*
Wolf, Nat. Biotechnol. 20, 768-769, 2002.*
Rosenberg et al, Science 287:1751, 2000.*
Song et al, Gene Therapy, 7(18):1527-1535, 2000.*
A. Morales, D. Eidinger, and A.W. Bruce; "Intracavitary *Bacillus* Calmette-Guerin in the Treatment of Superficial Bladder Tumors;" The Journal of Urology, 1976; pp. 180-183.
Peter D.J. Vegt, J. Alfred Witjes, Wim P.J. Witjes, Wim H. Doesburg, Frans M.J. Debruyne, and A.P.M. van der Meijden; "A Randomized Study of Intravesical Mitomycin C, *Bacillus* Calmette-Guerin Tice and *Bacillus* Calmette-Guerin RIVM Treatment in pTa-pT1 Papillary Carcinoma and Carcinoma in Situ of the Bladder;" The Journal of Urology, 1995; pp. 929-933.
Shin Suzuki, Nobuo Shinohara, Toru Harabayashi, Akihisa Taniguchi, Kazaunori Haga, Soshu Sato, Kazuya Sakamoto, Tomohiko Koyanagi; "Complications of *Bacillus* Calmette-Guerin Therapy in Superficial Urothelial Cancer: Clinical Analysis and Implications;" The Japan Society of Clinical Oncology, 2002; pp. 289-293.
Alvaro Morales, Joseph L. Chin, and Ernest W. Ramsey; "Mycobacterial Cell Wall Extract for Treatment of Carcinoma in Situ of the Bladder;" The Journal of Urology, 2001; pp. 1633-1638.

A. Böhle, A, Thanhäuser, A.J. Ulmer, M. Ernst, H.D. Flad, and D. Jocham; "Dissecting the Immonobiological Effects of *Bacillus* Calmette-Guerin (BCG) in Vitro: Evidence of a Distinct BCG-Activated Killer (BAK) Cell Phenomenon;" The Journal of Urology, 1993; pp. 1932-1937.
N.E. Stavropoulos, K. Hastazeris, I. Filladis, I. Mihailidis, E. Ioachim, Z. Liamis, and P. Kalomiris; "Intravesical Instillations of Interferon Gamma in the Prophylaxis of High Risk Superficial Bladder Cancer;" Taylor and Francis healthsciences, 2002; pp. 3218-3222.
Donald L. Lamm, Dale R. Riggs, Jean I. Dehaven, and Randall W. Bryner; "Immunotherapy of Murine Bladder Cancer by Irradiated Tumor Vaccine;" The Journal of Urology, 1991; pp. 195-198.
Chi-Feng Lee, Sun-Yran Chang, Dar-Shih Hsieh, and Dah-Shyong Yu; "Immunotherapy for Bladder Cancer Using Recombinant *Bacillus* Calmette-Guerin DNA Vaccines and Interleukin-12 DNA Vaccine;" The Journal of Urology, 2004; pp. 1343-1347.
Dah-Shyong Yu, Chi-Feng Lee, Dar-Shih Hsieh, and Sun-Yran Chang; "Antitumor Effects of Recombinant BCG and Interleukin-12 DNA Vaccines on Xenografted Murine Bladder Cancer;" Elsevier Inc, 2004; pp. 596-601.
Chi-Feng Lee, Sun-Yran Chang, Dar-Shih Hsieh, and Dah-Shyong Yu; "Treatment of Bladder Carcinomas Using Recombinant BCG DNA Vaccines and Electroporative Gene Immunotherapy;" Cancer Gene Therapy, 2004; pp. 194-207.
Georg Widera, Melissa Austin, Dietmar Rabussay, Cheryl Goldbeck, Susan W. Barnett, Minchao Chen, Louisa Leung, Gillis R. Otten, Kent Thudium, Mark J. Selby, and Jeffrey B. Ulmer; "Increased DNA Vaccine Delivery and Immunogenicity by Electroporation in Vivo;" The American Association of Immunologists, 2000; pp. 4635-4640.
Hai L. Wang, Li Y. Tsai, and Eminy H.Y. Lee; "Corticotropin-Releasing Factor Produces a Protein Synthesis-Dependent Long-Lasting Potenation in Dentate Gyrus Neurons;" The American Physiological Society; pp. 343-349.
Mina Morimura, Osamu Ishiko, Toshiyuki Sumi, Hiroyuki Yoshida, and Sachio Ogita; "Angiogenesis in Adipose Tissues and Skeletal Muscles with Rebound Weight-Gain After Diet-Restriction in Rabbits;" International Journal of Molecular Medicine, 2001; pp. 499-503.

* cited by examiner

*Primary Examiner*—Thaian N Ton
(74) *Attorney, Agent, or Firm*—Thomas, Kayden, Horstemeyer & Risley

(57) ABSTRACT

A plurality of DNA cancer vaccines and their uses in treating cancer are disclosed. Genes encoding *Mycobacterium bovis bacillus* Calmette-Guérin (*M. bovis* BCG) recombinant antigens and genes encoding interleukin-12 heterodimer were respectively cloned into eukaryotic expression vectors to express the encoded recombinant proteins in mammalian cells in vivo whereby specific immune responses are evoked and are effective in preventing, attenuating and/or suppressing the growth of a tumor.

14 Claims, 8 Drawing Sheets
(5 of 8 Drawing Sheet(s) Filed in Color)

DNA CANCER VACCINES

BACKGROUND

1. Field of the Invention

The present invention relates to DNA vaccines and theirs uses in treating cancers. More particularly, the present invention relates to DNA vaccines for treating solid tumors such as bladder cancer, lung cancer, prostate cancer, melanoma and kidney cancer.

2. Description of Related Art

A vaccine is one of the most effective, safe, nontoxic and economical ways to prevent disease and to control the spreading of disease. Conventional vaccines are a form of immunoprophylaxis given before disease occurrence to afford immunoprotection by generating a strong host immunological memory against a specific antigen. The primary aim of vaccination is to activate the adaptive specific immune response, primarily to generate B and T lymphocytes and/or natural killer cells (NK cells) against specific antigen(s) associated with the disease.

Similarly, cancer vaccines aim to generate immune response against cancer tumor associated antigens. Cancers can be immunogenic and can activate host immune response capable of controlling the disease and causing tumor regression. Many protein/glycoprotein tumor-associated antigens have been identified and linked to certain types of cancer, such as MAGE-3, MAGE-1, gp100, TRP-2, ras, β-catenin, gp43 and HSP-70, just to name a few.

There is a report regarding the successful use of live *Mycobacterium bovis bacillus* Calmette-Guérin (M. BCG) in preventing the progression and recurrence of superficial bladder cancer after transurethral resection of the bladder tumor (see Morales A. et al., "Intracavitary *bacillus* Calmette-Guérin in the Treatment of superficial Bladder Tumors", (1976) *J. Urol.* 116:180-183). However, this approach has not been completely satisfactory due to a number of problems, for example, it is not effective to all patients, a significant 30-40% of patients either does not respond to BCG therapy or shows adverse side effects such as fever, granulomatous prostatitis, pneumonitis, hepatitis and BCG sepsis (see Vegt P. D. et al., "*Bacillus* Calmette-Guérin Tice and *Bacillus* Calmette-Guérin RIVM treatment in pTa-pT1 papillary carcinoma and carcinoma in situ of the bladder", (1995) *J. Urol.* 153:929-933; Suzuki S. et al., "Complications of *Bacillus* Calmette-Guérin Therapy In Superficial Urothelial Cancer: Clinical Analysis And Implications", (2002) *Int. J. Clin. Oncol.* 7:289-293). The use of nonviable heat-inactivated BCG and BCG subfractions in reducing adverse effects caused by BCG therapy has also been suggested (see Morales et al, "Mycobacterial Cell Wall Extract For Treatment of Carcinoma in situ of the Bladder", (2001) *J. Urol.* 166:1633-1637), whereas others point out that treatments with viable organisms is more effective (see Bohle et al, "Dissecting the Immunobiological Effects of *Bacillus* Calmette-Guérin (BCG) In Vitro: Evidence of a distinct BCG-activated Killer (BAK) Cell Phenomenon", (1993) *J. Urol.* 150:1932-1937). According to the results of a recent study, combination of BCG therapy and the activation of cytokines pathways within a host to generate interferon such as interferon α-2b, interleukin-2, and interferon α may further enhance the efficacy of BCG therapy without increasing its adverse effects (see Stavropoulos et al., "Intravesical Instillations of Interferon γ In The Prophylaxis of High Risk Superficial Bladder Cancer—Results of A Controlled Prospective Study", (2002) *J. Urol. Nephrol.* 36:218-222). Unfortunately, the development of a tumor vaccine based on this approach has failed (see Lamm et al., "Immunotherapy Of Murin Bladder Cancer By Irradiated Tumor Vaccine", (1991) *J. Urol.* 145:195-198). Therefore, there exists a need for developing an improved DNA cancer vaccine, which is more potent than the current BCG immunotherapy and without its adverse side effects, for the treatment of mammalian cancers, especially human bladder cancer (see Lee et al., "Immunotherapy for bladder cancer using recombinant BCG DNA Vaccines and Interleukin-12 DNA Vaccine", (2004) *J. Urol.,* 171:1343-1347; see Yu et al., Antitumor effects of recombinant BCG and interleukin-12 DNA Vaccines on the xenografted murine bladder cancer (2004) *Urology,* 63:596-601; see Lee et al., "Treatment of bladder carcinomas using recombinant BCG DNA Vaccines and electroporative gene immunotherapy", *Cancer Gene Ther* (2004) 11:194-207).

SUMMARY

It is therefore the objectives of the present invention to provide methods and compositions for immunizing against tumor-associated antigens, suppressing or attenuating tumor growth, and treating cancers. The methods and compositions provided may induce antigen-mediated local production of cytokines and stimulated accumulation of inflammatory cells through CD4+, CD8, or other T cell subsets.

The compositions provided in the present invention are comprised of DNA vaccines; each DNA vaccine comprises nucleic acid encoding at least two recombinant BCG antigens. These BCG antigens include Ag85A, Ag85B, PstS3, Mpt64, and ESAT6. These antigens may be further chimeric with other molecules, immunogenic peptides and/or helper antigen peptides. The DNA vaccines may further include other components that help direct the nucleic acid to a certain location in the cell or direct translation of the recombinant BCG antigens.

It is therefore an objective of the present invention to provide a DNA cancer vaccine for treating cancers comprises a first plasmid vector comprising a polynucleotide sequence encoding at least two recombinant BCG antigens operably linked to transcription regulatory elements, wherein upon administration to a mammal, said DNA cancer vaccine can effectively attenuate or suppress the growth of cancer cells.

It is another objective of the present invention to provide a DNA cancer vaccine comprises a plasmid vector comprising a polynucleotide sequence encoding a heterodimeric protein of Interleukin-12 (mIL-12) operably linked to transcription regulatory elements, wherein upon administration to a mammal, said DNA vaccine can effectively attenuate or suppress the growth of cancer cells.

It is still another objective of the present invention to provide a composition for treating cancers comprising at least four recombinant DNA cancer vaccines prepared according to the method of this invention, wherein each of said DNA cancer vaccines comprises a first plasmid vector comprising a polynucleotide sequence encoding at least two BCG antigens, which can increase the activities of T cells and/or macrophages of the host. Upon administrating to a mammal, the composition of the present application can induce proliferation of the T cells and/or macrophages within the host mammal, and thereby effectively attenuates or suppresses the growth of cancer cells. The composition of the present invention may further comprise an additional DNA cancer vaccine, which comprises a second plasmid vector comprising a polynucleotide sequence encoding a heterodimeric protein of Interleukin-12. The additional DNA cancer vaccine serves in activating the cytokine pathways of the host mammal, and thereby acts synergistically with said composition comprising at least four recombinant BCG DNA cancer vaccines in preventing and/or attenuating the growth of cancer cells.

It is thus another objective of the present invention to provide a method for preventing recurrence of cancers and/or treating cancers, comprising the step of administrating the composition prepared according to the method of this invention to a mammal in need of such treatment, wherein said composition comprising at least four recombinant DNA cancer vaccines prepared according to the method of this invention, wherein each of said DNA cancer vaccines comprises a first plasmid vector comprising a polynucleotide sequence encoding at least two BCG antigens, which can increase the activities of T cells and/or macrophages of the host. Upon administrating to a mammal, the composition of the present application can induce proliferation of the T cells and/or macrophages within the host mammal, and thereby effectively attenuates or suppresses the growth of cancer cells. The composition of the present invention may further comprise an additional DNA cancer vaccine, which comprises a second plasmid vector comprising a polynucleotide sequence encoding a heterodimeric protein of Interleukin-12. The additional DNA cancer vaccine serves in activating the cytokine pathways of the host mammal, and thereby acts synergistically with said composition comprising at least four recombinant BCG DNA cancer vaccines in preventing and/or attenuating the growth of cancer cells.

The DNA cancer vaccines of this invention may be administered concurrently with chemotherapeutic agents such as cisplatin, 5-fluorouracil, vinblastine and adriamycin.

The DNA cancer vaccines of this invention may be administered subcutaneously, intradermally, intramuscularly or electroporationally into an organ. The vaccines are administered in a way that induces a host normal cell to express the recombinant BCG antigens.

The details of one or more embodiments of the invention are set forth in the accompanying description and drawings below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Figures 1A, 1B, 1C:
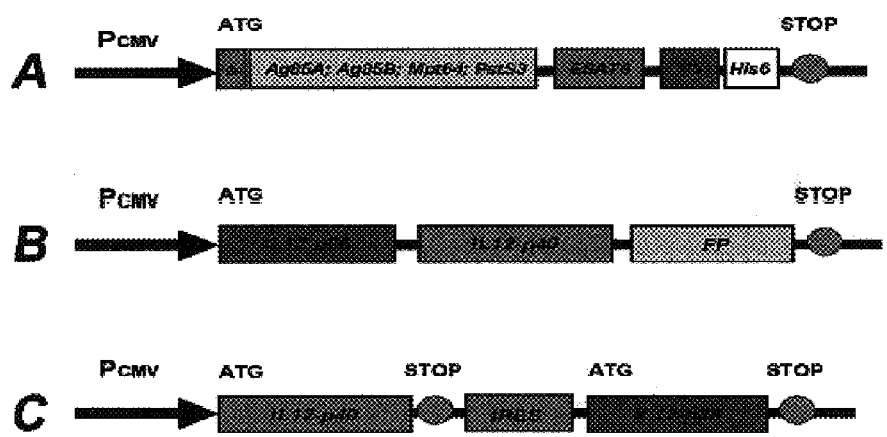
FIG. 1 is the schematic drawing showing the expression system of poly-rBCG used in the four vaccines and the mIL-12 used in the fifth vaccine as adjuvant, (a) constructs of poly-rBCG DNA vaccines (pCMV-AE, pCMV-BE, pCMV-ME and pCMV-PE); (b) single chain mIL-12 DNA fused with FP genes (pEYFP-p35p40); (c) bicistronic mIL-12 DNA vaccine (pIRES-p35p40) contained within the internal ribosome entry site (IRES)
Figure 2:
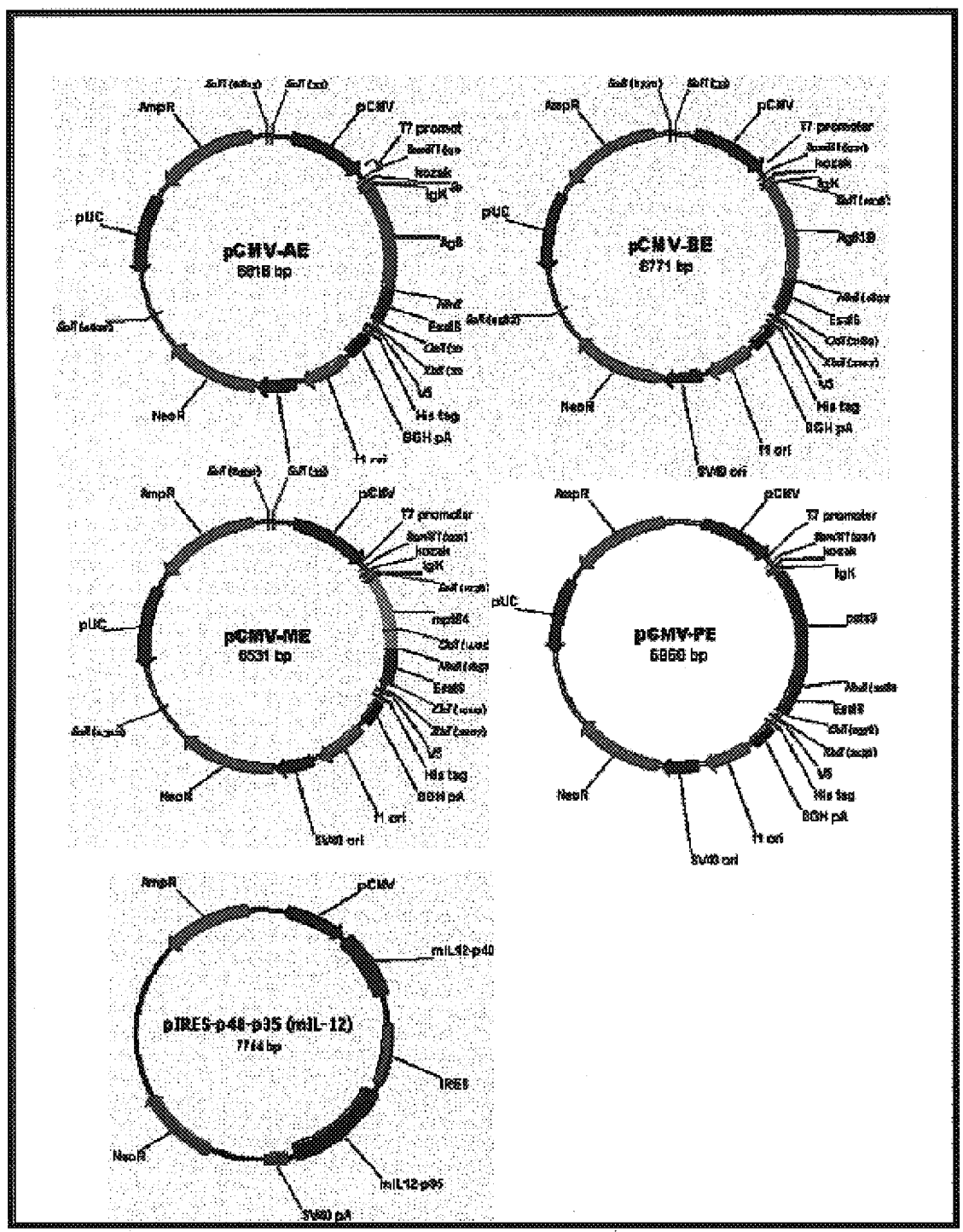
FIG. 2 illustrates the maps for various restriction sites of the DNA cancer vaccines of this invention.

The practices of this invention are hereinafter described in detail with respect to the production of DNA vaccines and the treatment of bladder cancers. However, the practices of this invention are also applicable to the production of a lung cancer vaccine, a prostate cancer vaccine, a melanoma vaccine or a kidney cancer vaccine, particularly infectious disease caused by bacteria, fungi and other microorganisms.

The invention provides an improved efficient design for delivering recombinant BCG DNA vaccines in vivo to immunize the host and thereby providing protective immunity to vertebrates, including humans, against cancers. The invention provides methods and compositions for immunizing with recombinant BCG antigens, suppressing or attenuating the growth of cancers, preventing recurrence of cancers and treating cancers. The methods and compositions provided may induce antigen-mediated local production of cytokines and stimulated accumulation of inflammatory cells through CD4+, CD8, or other T cell subsets.

This invention provides polynucleotides, which when directly introduced into a vertebrate in vivo, including mammals, such as human, induces the expression of encoded proteins within the animal. As used herein, a polynucleotide is a nucleic acid, which contains essential regulatory elements such that upon introduction into a living vertebrate cell, is able to direct the cellular machinery to produce translation products encoded by the genes comprising the polynucleotide and present the translation products to the inoculated animal's immune system such that protective immunity is provided.

In one embodiment of the invention, the polynucleotide of the invention, the polynucleotide is a polydeoxyribonucleic acid comprising genes for at least two M. Bovis BCG antigens operably linked to transcriptional regulatory elements. By the term "operably linked to transcriptional regulatory elements" is meant that a polypeptide coding sequence and transcriptional and translational controlling sequences are connected in such a way as to permit polypeptide expression when the appropriate molecules (e.g., transcriptional activation proteins) are bound to the regulatory sequence. In another embodiment of this invention, the polynucleotide of the invention, the polynucleotide is a polydeoxyribonucleic acid comprising gene for Interleukin-12 operably linked to transcriptional regulatory elements. When the polynucleotides of the invention are introduced into a host, one or more recombinant protein products encoded by the polynucleotides that normally do not exist in the host are transcribed, and are activated to launch a protective immune response (i.e., the helper T lymphocytes response and activation of cytokines pathway). Because these exogenous recombinant proteins are produced by the host's own tissue, the expressed proteins are processed by the major histocompatibility system in a fashion analogous to when an actual M. BCG infection occurs. The result, as shown in this disclosure, is induction of immune response against M. BCG. Polynucleotides for the purpose of generating immune response to an encoded protein are referred to herein as DNA vaccines.

There are many embodiments of this invention, which those skilled in the art can appreciate from the specification. Thus, different transcriptional promoters, terminators, carrier vectors or specific gene sequences may be used successfully.

The instant invention provides a method of using a polynucleotide, which upon introduction into a mammalian tissue introduces the expression, in vivo, of the polynucleotide, thereby producing the encoded gene product. The encoded antigens can be translation products or polypeptides. The polypeptides can be of various lengths, and can undergo normal host cell modifications such as glycosylation, myristoylation, or phosphorylation. It is readily apparent to those skilled in the art that variations or derivatives of the nucleotide sequence encoding a protein can be produced, which alter the amino acid sequence of the encoded protein. The altered expressed protein may have an altered amino acid sequence, yet still elicits immune responses that react with the mycobacterial protein, and are considered functional equivalents. In addition, fragments of the full-length genes that encode proteins of the full-length protein may also be constructed. These fragments may encode a protein or peptide that elicits antibodies which react with the mycobacterial protein, and are considered functional equivalents.

In one embodiment of this invention, a polynucleotide encoding at least two *M. Bovis* BCG antigens is incorporated in an expression vector. These *M. Bovis* BCG antigens include Ag85A, Ag85B, PstS3, Mpt64, and ESAT6. The nucleic acid sequences of these *M. Bovis* BCG antigens are known and can be obtained from GenBank. The selected *M. Bovis* BCG antigen genes were amplified by polymerase chain reactions (PCR) and the amplified DNA fragments were purified, ligated and subcloned into an eukaryotic expression vector, wherein ESAT6 gene is ligated to the 3'-end of Ag85A, Ag85B, Mpt64, PstS3 genes, respectively. These antigens may be further chimeric with mouse immunoglobulin kappa (IgK) chain leader sequence. The vector contains a transcriptional promoter recognized by eukaryotic RNA polymerase, and a transcriptional terminator at the end of Mycobacterial genes coding sequence, in particular, pCMV-V5-His6 (available from Clontech Laboratories (Palo Alto, Calif.). The methods used in producing the expression vectors may be accomplished by methods known by those skilled in the art.

In another preferred embodiment of this invention, a polynucleotide encoding a heterodimeric protein of Interleukin-12 (m-IL) is incorporated in an expression vector. Murine interleukin-12 subunits, such as 35-kDa light chain (p35) and 40-kDa heavy chain (p40), were amplified and cloned into a vector containing an internal ribosome entry site (IRES) for the expression of bicistronic mRNA of m-IL p35 and m-IL p40. The methods used in producing a heterodimeric protein by IRES-expression vectors are well known in the art.

The protective efficacy of *M. Bovis* BCG antigens against cancer is demonstrated by immunization with the DNA vaccines prepared by methods of this invention. The inoculation of DNA vaccines may result in the generation of significant protective immunity against cancers. In particular, helper T lymphocyte responses and activation of cytokines pathway are produced. In a preferred embodiment of this invention, a composition for preventing and/or treating cancer is provided. The composition comprises at least four DNA vaccines, wherein each of said DNA vaccines comprises a first plasmid vector comprising a polynucleotide sequence encoding mycobacterial antigens selected from the group consisting of Ag85A, Ag85B, PstS3, Mpt64, and ESAT6. The composition may further comprise an addition DNA cancer vaccine (i.e., the fifth DNA vaccine) comprises a second plasmid vector comprising a polynucleotide sequence encoding a heterodimeric protein of m-IL 12.

Chemotherapeutically effective agents such as cisplatin, 5-fluorouracil, vinblastine and adriamycin may be administered prior to, during, or subsequently after the administration of the DNA vaccines of this invention.

The amount of expressed DNA or transcribed RNA to be introduced into a vaccine recipient will have a very broad dosage range and may depend on the strength of the transcriptional and translational promoters used. In addition, the magnitude of the immune response may depend on the level of protein expression and on the immunogenicity of the expressed gene product. In general, an effective dose ranges of about 1 ng to 5 mg, 100 ng to 2.5 mg, 1 μg to 750 μg, and preferably about 10 μg to 300 μg of DNA vaccine is administered directly into tissue. The DNA vaccine of this invention can be administered or inoculated, subcutaneously, intramuscularly, intradermally, or by other modes such as intraperitoneal, intravenous, or inhalation, in the presence of adjuvants or other substances that have the capability of promoting DNA uptake or recruiting immune system cells to the site of inoculation. The chosen route of administration will depend on the vaccine composition and the disease status of patients. Relevant considerations include the types of immune cells to be activated, the time which the antigen is exposed to the immune system and the immunization schedule. It is also contemplated that booster vaccinations may be provided. DNA vaccines directed to *M. Bovis* BCG antigens and/or heterodimeric m-IL 12 proteins can be administered sequentially or concurrently.

The polynucleotide may be naked, that is, unassociated with any proteins, adjuvants or other agents which affect the recipients' immune system. In this case, it is desirable for the polynucleotide to be in physiologically acceptable solution, such as, but not limited to, sterile saline or sterile buffered saline. Alternatively, the DNA may be associated with liposomes, such as lecithin liposomes or other liposomes known in the art; or the DNA may be associated with an adjuvant known in the art to boost immune responses, such as a protein or other carrier. Agents which assist in the cellular uptake of DNA, such as, but not limited to, calcium ions, may also be used. These agents are generally referred to herein as pharmaceutically acceptable carriers. For DNA vaccines intended for human use, it is useful to have the final DNA product in a pharmaceutically acceptable carrier or buffered solution. Pharmaceutically acceptable carriers or buffered solutions are known in the art and include those described in a variety of text such as Remington's Pharmaceutical Sciences.

There are several advantages of immunization with a gene rather than its gene product. The first is the relative simplicity with which native or nearly native antigen can be presented to the immune system. A second advantage of DNA immunization is the potential for the immunogen to enter the MHC class I pathway and evoke a cytotoxic T cell response. Immunization with DNA vaccines of this invention elicited a cytotoxic T cell response (such as CD4+, CD8, and F4/80 macrophages cell markers) as well as production of various cytokines.

The vaccines of the present invention are useful for administration to mammals, including but not limited to, pigs, cattle, horses, sheep, rabbits, cats, dogs, mice, rats, and primates such as monkeys. The techniques for administering these vaccines to animals and humans are known to those skilled in the relevant arts.

The following examples are provided to illustrate the present invention without, however, limiting the same thereto.

EXAMPLES

Example 1

Preparation of Vectors for DNA Vaccines

1. Preparation vectors containing *M. bovis* BCG antigen nucleic acid sequences (recombinant BCG DNA vaccines) The human mycobacterial genomic DNA (*M. bovis* BCG) was used as a polymerase chain reaction (PCR) template to produce copies of the Ag85A, Ag85B, Mpt64, PstS3 and ESAT6 genes. The nucleic acid sequences of these BCG antigens are known and can be obtained from GenBank with access number of AY207395, AY207369, AY208674, AY207397 and AY207398 for Ag85A, Ag85B, Mpt64, PstS3 and ESAT6 gene, respectively. PCR was performed with gene-specific primers (see Table 1) for 30 cycles, and each cycle consisted of 15 sec at 94° C., 1 min at 56° C., and 2 min at 72° C. These DNA fragments were purified and ligated into a pCRII-TOPO vector (Invitrogen Life Technologies), and then subcloned into the eukaryotic expression vector pCMV-V5-His6 (Clontech Laboratories, Palo Alto, Calif.). The ESAT6 gene was ligated to the 3'-end of each of the other four genes (i.e., Ag85A, Ag85B, Mpt64, and PstS3). All genes encoding antigens were fused to a mouse immunoglobulin kappa (IgK) chain leader sequence and amplified with a 5' primer containing a SalI restriction site and a 3' primer designed with a NheI site.

2. Preparation of vectors containing murine interleukin-12 (mIL-12) 35-kDa light chain (p35) and 40-kDa heavy chain (p40) nucleic acid sequences (heterodimeric mIL-12 DNA vaccine) The mIL-12 35-kDa light chain (p35) and 40-kDa heavy chain (p40) were amplified from cDNA library of $C_3H$/HeN mouse spleen cells. The positive clones were inserted into the pIRES vector (Clontech Laboratories, Palo Alto, Calif.), which is a mammalian expression vector that allows expression of two genes of interest at high levels by cloning IL-12 p40 and IL-12 p35 into two cloning sites. This permits both the genes of interest to be translated from a single biscistronic mRNA. To construct the mIL-12 vaccine fusion with fluorescent protein (FP), these genes of p35, p40 (p35 and p40 are peptides subunits of mIL-12) and p35p40 (p35p40 is a single-chain peptide of mIL-12) were ligated to the plasmid vectors pEGFP-N1, pERFP-N1 and pEYFP-N1 (Clontech Laboratories, Palo Alto, Calif.), respectively. All constructs were used in expression studies in vivo. FIG. 1 schematically illustrates the design of three expression systems: the eukaryotic poly recombinant BCG (poly-rBCG) system (FIG. 1A), and the heterodimeric mIL-12 system with or without FP on the C-terminal end (FIGS. 1B and 1C). FIG. 2 shows the maps for various restriction sites of the DNA cancer vaccines of this invention.

TABLE 1

Primer sequences for DNA cancer vaccines

| Gene and Orientation | Primer Sequence (5'→3') |
|---|---|
| Ag85A[a] | |
| Sense | 5'-GTC GAC TTT TCC CGG CCG GGC TTG-3' (SEQ ID NO. 1) |
| Antisense | 5'-GCT AGC GTC TGT TCG GAG CGA GGC G-3' (SEQ ID NO. 2) |
| Ag85B[a] | |
| Sense | 5'-GTC GAC TTC TCC CGG CCG GGG CTG-3' (SEQ ID NO. 3) |
| Antisense | 5'-GCT AGC GCC GGC GCC TAA CGAACT C-3' (SEQ ID NO. 4) |
| Mpt64[a] | |
| Sense | 5'-CGCG GTC GAC GCG CCC AAG ACC TAC TGC-3' (SEQ ID NO. 5) |
| Antisense | 5'-CCGG GCT AGC GGC CAG CAT CGA GTC GAT C-3' (SEQ ID NO. 6) |
| PstS3[a] | |
| Sense | 5'-CCGT CTC GAG TGT GGT AAC GAC GAC AAT GTG-3' (SEQ ID NO. 7) |
| Antisense | 5'-GCGG GCT AGC GGC GAT CGC GTT GAC CGC-3' (SEQ ID NO. 8) |
| ESAT6[b] | |
| Sense | 5'-CGGC GCT AGC ATG ACA GAG CAG CAG TGG-3' (SEQ ID NO. 9) |
| Antisense | 5'-CC ATC GAT TGC GAA CAT CCC AGT GAC G-3' (SEQ ID NO. 10) |
| Ig κ[c] | |
| Sense | 5'-CAC ACC ATG GAT TTT CAA GTG CAG AT-3' (SEQ ID NO. 11) |
| Antisense | 5'-GCT AGC CTA GTG CCA TGG TGT CGA CTC CTC TGG ACA TTA TGA GTG-3' (SEQ ID NO. 12) |
| mIL-12-p35[d] | |
| Sense | 5'-TCTAGA GCT AGC ATG TGT CAA TCA CGC TAC-3' (SEQ ID NO. 13) |
| Antisense | 5'-GTCGAC GGC GGA GCT CAG ATA GCC-3' (SEQ ID NO. 14) |

TABLE 1-continued

Primer sequences for DNA cancer vaccines

Gene and Primer Sequence
Orientation (5'→3')

mIL-12-p40[d]
   Sense    5'-GCTAGC GCT AGC ATG TGT CCT CAG AAG
             CTA-3' (SEQ ID NO. 15)

Antisense 5'-CTCGAG GGA TCG GAC CCT GCA
             GGG-3' (SEQ ID NO. 16)

[a]Primers design based on the conserved sequence of *Mycobacterium tuberculosis* with genes encoding Ag85A, Ag85B, Mpt64 and PstS3 were facilitated to fuse with a mouse Ig κ chain sequence and ESAT6, amplified with a 5' primer containing a Sa/I restriction site and a 3' primer designed with a NheI site.
[b]Primers design based on the conserved sequence of *Mycobacterium tuberculosis* with genes encoding ESAT6, amplified with a 5' primer containing a NheI restriction site and a 3' primer designed with a XbaI site.
[c]Primers design based on the murine immunoglobulin kappa (Ig κ) chain sequence. Amplified with a 5' end primer containing a KOZAK consensus sequence upstream of the initiator ATG codon, and 3' primer was designed with XhoI resitriction site for p40. Amplified with a 5' end primer containing a XbaI restriction site, and 3' primer was designed with stop codon and Sa/I restriction site for p35.

Example 2

In Vivo Transfection/Inoculation of DNA Vaccines in Tumors and Muscle Tissues

1. In Vivo Transfection/Inoculation of poly-BCG Vaccines or mIL-12 Vaccines in Tumors and Muscle Tissues Four rBCG DNA vaccines (plasmids coding for five immunogenic mucobacterial antigens and the mouse Ig κ signal sequence) and heterodimeric mIL-12 DNA vaccine (pIRES-p40p35) were used. Briefly, 4- to 6-week-old femal $C_3H/HeN$ mice were anesthetized in groups of 8 with an intraperitoneal injection of ketamine HCl/xylazine (100 μg/15 μg per mouse) before plasmid injection and electroporation. For the transfer of poly-rBCG intratumoral genes, MBT-2 cells (approximately $5\times10^6$ cells) were subcutaneously inoculated into the back of 5-week-old female $C_3H/HeN$ mice, and tumors were allowed to develop for about 2 weeks. The tumors were then excised and chopped into small pieces, and equal amounts of tumor were subcutaneously inoculated into the right flank of 6-week-old mice. Then, 1 to 2 weeks after inoculation, when the tumors were about 5-7 mm in diameter, 30 μg of each naked mycobacterial DNA vaccine in 120 μl of normal saline solution were injected intratumorally with a syringe. For the intramuscular transfer of mIL-12 genes, the quadriceps femoris muscles of 6-week-old female $C_3H/HeN$ mice were injected with 100 μg of mIL-12 vaccines, respectively. Negative control mice were injected with the empty vector only.

2. Electroporation Transfection To improve the DNA transfer efficiency, electroporation was performed according to the process disclosed by Widera et al., ("Increased DNA vaccine delivery and immunogenicity by electroporation in vivo", *J. Immunol.* (2000) 164:4635-4640) and Lee et al., ("Treatment of bladder carcinomas using recombinant BCG DNA Vaccines and electroporative gene immunotherapy", *Cancer Gene Ther.* (2004) 11:194-207) which was followed at the site of each injection. Briefly, two-needle-array electrodes (BTX, San Diego, Calif.) were inserted into the tumor masses or muscle fibers immediately after DNA injection. The distance between the electrodes was 5 mm, and the array was inserted longitudinally relative to the tumor masses or muscle fibers. Electric pulses were generated with a square-wave electroporator (model 830, BTX). In vivo electroporation parameters were as follows: distance between the electrodes, 100V/cm; pulse duration, 50 msec; and 10 pulses with reversal of polarity. These electroporation parameters were selected on the basis of previous reports and our preliminary experiments, and are varied according to the animal species, dose of the vaccines to be delivered and size of the tumor. Any skilled person in this art may determine the suitable parameters for any selected application depends on the factors described above without undue experiments.

3. In Vivo Co-Transfection/Co-Inoculation of poly-BCG vaccines and mIL-12 vaccines Similarly, co-transfection and/or co-inoculation of poly-BCG vaccines and mIL-12 vaccines was accomplished by the method described above, except poly-BCG vaccines and mIL-12 vaccines were administered at the same time or sequentially.

4. Results The expression efficiency of the delivered DNA vaccines were determined by fluorescence imaging analysis and RT-PCR.

Figure 3A:
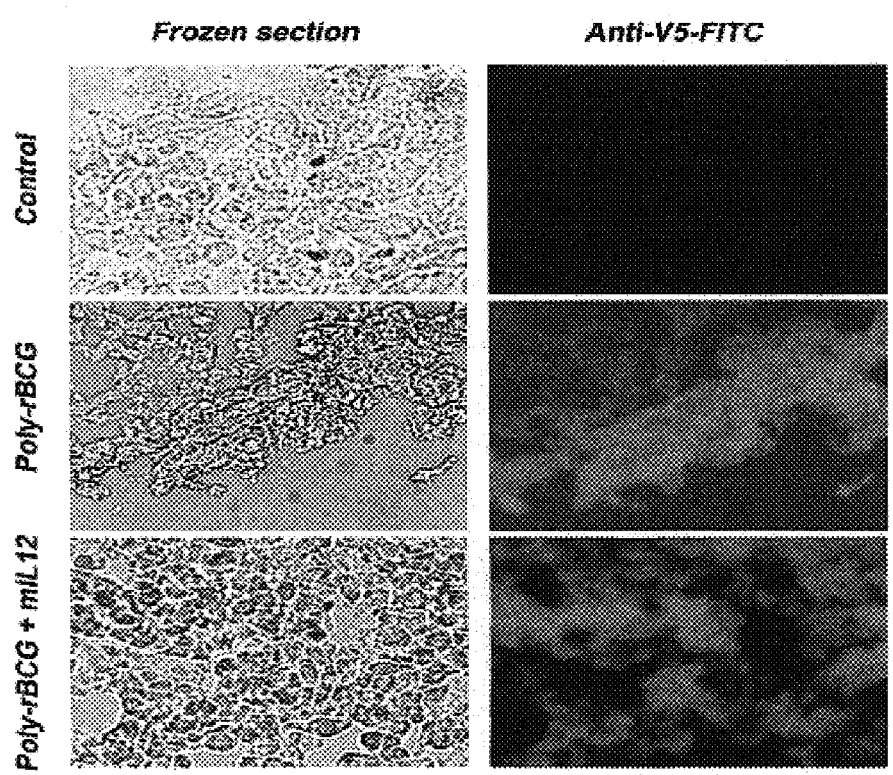
FIG. 3 illustrates the expression of poly-rBCG in bladder tumor and mIL-12 in quadriceps femoris muscle via electroporative gene immunotherapy (EPGIT) in vivo, (A) protein expression of poly-rBCG determined by FITC fluorescence microscopy (magnification, 60×); (B) protein expression and co-localization of mIL-12 pEGFP-p40, pERFP-p35, and pEYFP-p35p40 in the quadriceps femoris muscle, measured by confocal microscopy (bar is 20 µm; magnification, 40×); (C) the mRNA level of Ag85A, Ag85B, Mpt64, PstS3 and ESAT6 genes in the tumor mass determined by RT-PCR, significant difference from β-actin control is represented by an asterisk (*, $p<0.05$) according to one preferred embodiment of this invention.
Figure 3B:
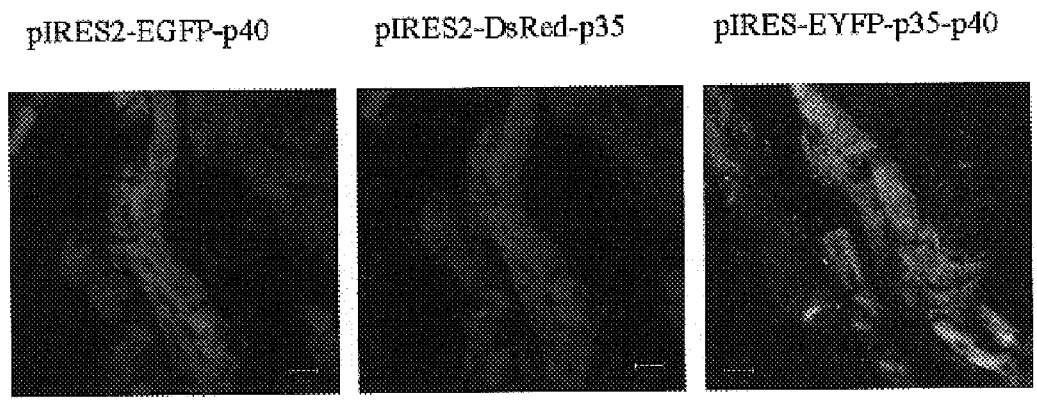

4.1 Detection of the Expressed DNA Vaccines by FITC-fluorescence Microscopy. Poly-rBCG DNA vaccines containing V5-His6 tag were detected in freeze-sectioned bladder tumors 5 μm thick) by staining with antibody to V5-fluorescein isothiocyanate (FITC) monoclonal antibody (Invitrogen Life Technologies) according to manufacturer's directions. Briefly, about 7 days after electroporative gene immunotherapy (EPGIT) with either the empty control vector alone or with the four combined recombinant mycobacterial DNA vaccines fused with a V5-His6 tag or co-expressed mIL-12, mice (n=6) were sacrificed. Their tumors were harvested, fixed in 10% paraformaldehyde, stained with FITC-labeled anti-V5 monoclonal antibody (Invitrogen Life Technologies), and viewed under a fluorescence microscope (Xenon arc lamp and FITC filter on a Zeiss Axioskop). Images were acquired with a color charge-coupled-device camera and frame-grabbing equipment. To determine an expression rate, the expression efficiency of the electroporation-mediated poly-rBCG genes was measured by performing flow cytometric analysis with a FACSCalibur instrument to detect tumor cells expressed mycobacterial antigens fused with the V5-His tag. On the basis of staining results with various FITC-labeled anti-V5 and Biotin-labeled anti-His monoclonal antibodies (Invitrogen Life Technologies), cells positive for poly-rBCG were gated into different groups of MBT-2 cell populations. To demonstrate the expression of mIL-12 in the muscle cells, mice (n=5, treatment group) were sacrificed about 7 days after electroporation of recombinant mIL-12 DNA fused with either the EGFP, ERFP or EYFP plasmids. Their quadriceps femoris muscles were sectioned fresh (without freezing or fixation) into 5-μm-thick section and mounted in PBS for immediate confocal microscopy analysis. Confocal microscopy was performed on a Zeiss LSM510 system (Carl Zeiss, Jena, Germany). Images were directly imported into the Zeiss LSM510 software, and results were shown in FIG. 3. Compare with the negative control, the expression rate in mice vaccinated with poly-rBCG alone, or with combination of poly-rBCG and mIL-12 after 7 days was above 72% and 76%, respectively (FIG. 3A). The confocal images of the mice muscle tissues inoculated with mIL-12 DNA vaccines also showed that the p35, p40 and p35p40 subunits of mIL-12 are homogenously expressed in the mice muscle tissues (FIG. 3B).

Figure 3C:
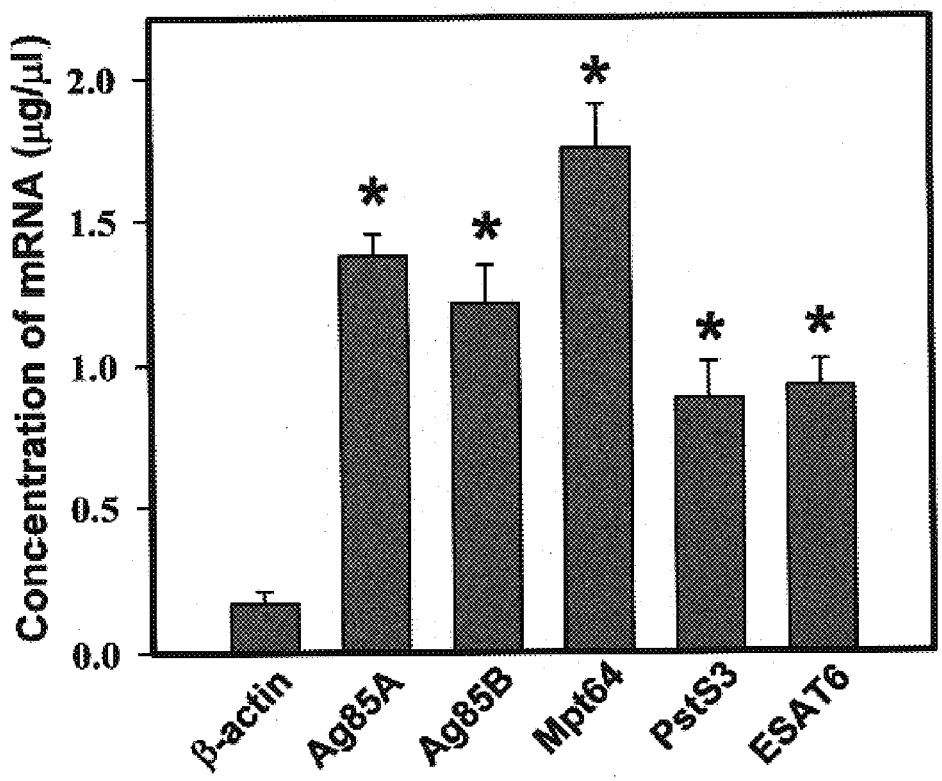

4.2 RT-PCR To determine individual expression of the mycobacterial genes, the RNA levels were examined by RT-PCR amplification. From lysates of bladder tumor cells transfected with poly-rBCG+mIL-12, total RNA was extracted with TRIzol (Gibco BRL, Grand Island, N.Y.) by following the manufacturer's directions. Then, RT-PCR was performed using the method described by Wang et al ("Corticotropin-releasing factor produces a protein synthesis-dependent long-lasting potentiation in dentate gyrus neurons", J Neurophysiol (2000) 83:343-349) to amplify Ag85A, Ag85B, Mpt64, PstS3, ESAT6, and β-lactin (internal control group) mRNAs. An initial denaturation of 1 min at 95° C. was followed by 25 cycles of denaturation at 94° C. for 30 s, annealing at 55° C. for 1 min, and extension at 72° C. for 2 min, followed by a final extension at 72° C. for 10 min. The expression levels of β-lactin, Ag85A, Ag85B, Mpt64, PstS3 and ESAT6 were 0.49±0.18, 1.19±0.08, 1.22±0.13, 1.75±0.16, 0.88±0.13 and 0.92±0.09 μg (FIG. 3C). These results confirmed active transcription of all recombinant BCG antigen genes and expression of all antigens encoded by them. The expression levels of mRNA between intratumorally transferred five-component poly-rBCG via EPGIT were significantly higher than that of internal control (n=5, $p<0.05$).

Example 3

Figure 4:
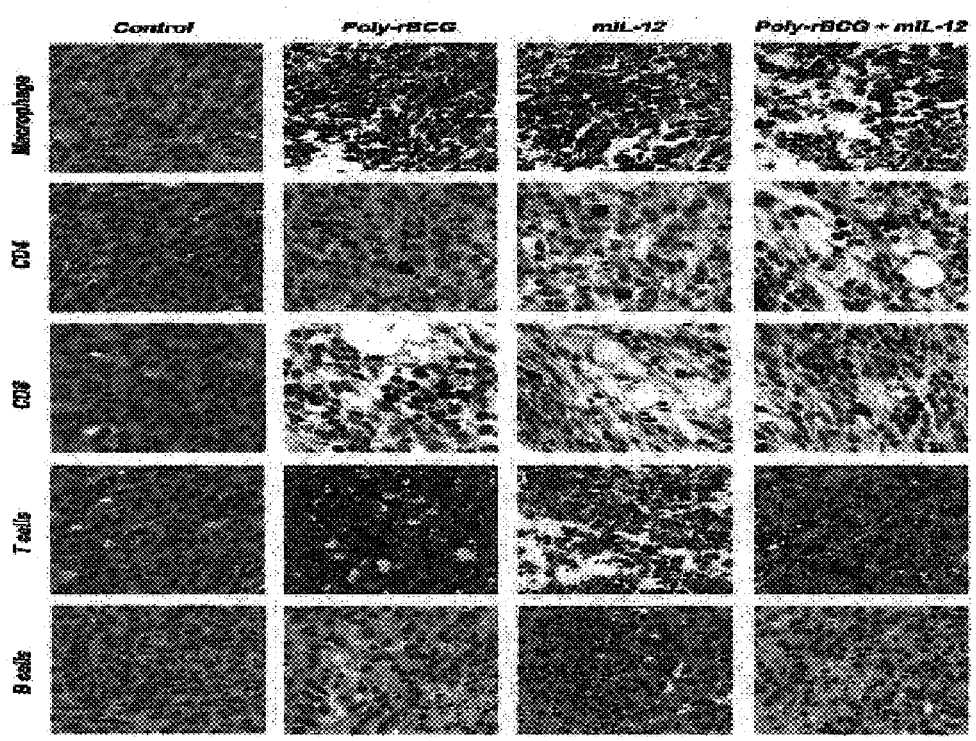
FIG. 4 illustrated the immunohistochemical analysis of cellular response in MBT-2 implants treated with empty vector, poly-rBCG, mIL-12, or poly-rBCG+mIL-12 according to one preferred embodiment of this invention: sections were stained with immunohistochemical staining by using specific antibodies to a macrophage marker (rat anti-mouse F4/80, a-d), CD4 lymphocyte marker (rat anti-mouse CD4, e-h), CD 8 lymphocyte marker (rat anti-mouse CD8a, i-l), T cell marker (hamster anti-mouse CD3e, m-p) or B cell marker (rat anti-mouse CD19, q-t)

Poly-rBCG DNA Vaccines Activate T-Cell Immune Response $C_3H$/HeN mice were first transplanted with MTB-2 tumor according to the procedure described in Example 2, and were then immunized via EPGIT with poly-rBCG vaccine, mIL-12 vaccine, poly-rBCG+mIL-12 vaccines or empty vector (i.e., pCMV-V5-His6 as the control group). The mice were then sacrificed on the 7th day after vaccination, and detection of T-cell markers (such as CD4 and CD8a), B-cell marker (such as CD 19) and macrophage (such as F4/80) was assessed in paraffin-embedded sections by using the avidin-biotin-peroxidase complex method described by Morimura et al (see Morimura et al., "angiogensis in adipose tissue after diet-restriction in rabbits", Int J Mol Med (2001) 8:499-503). Briefly, the 4-μm-thick sections were deparaffinized and then treated with 3.0% hydrogen peroxide (Sigma-Aldrich, St. Louis, Mo.) to block endogenous peroxidase activity. Subsequently, antigen retrieval procedures for formalin-fixed paraffin sections were performed by immersion of the slides in 1× ChemMate buffer for antigen retrieval (S2031; Dako, Kyoto, Japan) and by microwaving them at 700 W for 10 min. The protocol for LSAB2 kit peroxidase (Dako) was followed for each sample. The sections were blocked with 5% fetable bovine serum/PBS for 30 min and then incubated at room temperature with the CD4, CD8a, CD19 and F4/80 primary antibody 1:25 (BD PharMingen, San Diego, Calif.), respectively, followed by the secondary antibody 1:50 (BD PharMingen, San Diego, Calif.) for 90 min. Then, the samples were exposed to streptavidin-biotin-peroxidase complex and diaminobenzidine tetrachloride (Dako) as a chromogen, and they were counterstained with Mayer's hematoxylin. Sections of spleen and MBT-2 transferred with empty vector were used as positive and negative controls, respectively. The histochemical staining results are illustrated in FIG. 4.

In tumors treated with poly-rBCG, mIL-12, or poly-rBCG+mIL-12, the concentration of all markers increased except for the B-cell marker (FIG. 4), and for every markers that were monitored, the highest marker concentration was observed under the combined treatment of poly-rBCG and mIL-12, followed by poly-rBCG and mIL-12, with the induction of cell marker concentrations being the lowest under the treatment with mIL-12. Thus, all treatments appeared to elicit a cellular (Th1)-type response, rather than a humoral (Th2) response within MBT-2 implants.

Example 4 mIL-12 DNA Vaccines Activate Cytosolic Cytokine Pathway

Similarly, $C_3H$/HeN mice were first transplanted with MTB-2 tumor according to the procedure described in Example 2, and were then immunized via EPGIT with poly-rBCG vaccine, mIL-12 vaccine, poly-rBCG+mIL-12 vaccines or empty vector (i.e., pCMV-V5-His6 as the control group). Mouse serum (n=8) were collected on days 0, 7, 14 and 21 after vaccination, and cytokine CBA kit (cytometric Bead Array (CBA); BD Biosciences) was used to measure protein levels of IL-12, IL-4, IL-5, INF-γ and TNF-α according to the manufacturer's instructions. Briefly, 50 μl of serum and 10 μl of mixed CBA beads were added and incubated at room temperature for 2 hr, washed, and then incubated with a second cytokine phycoerythrin-labeled antibody per test. Flow cytometry was performed by using a dual-laser FACS-Calibur instrument (BD Biosciences) and data were displayed by using CellQuest software and analyzed with CBA analysis software (BD Biosciences). The expected sensitivity was in the pg/ml range. The data are the mean±SEM of the serum cytokine levels from the indicated groups.

Figure 5:
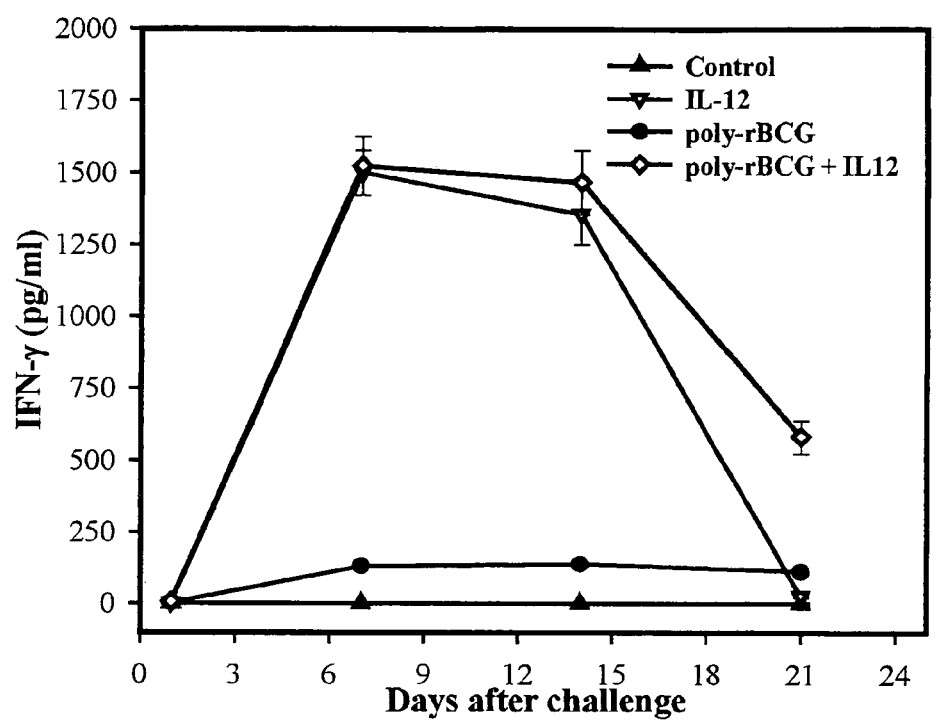
FIG. 5 illustrated the induction of INF-γ levels by DNA vaccines of this invention, four groups of mice (n=8 per group) were treated with vector, poly-rBCG, mIL-12, or poly-rBCG+mIL-12 vaccines, respectively according to one preferred embodiment of this invention vaccine.

Serum INF-γ level in mice treated with poly-rBCG vaccine alone gradually rose after vaccination and then stayed at a steady low level throughout the experiment. On the contrary, serum INF-γ level in mice treated with mIL-12 alone and the combination of poly-rBCG and mIL-12 increased sharply after vaccination and peaked on the $7^{th}$ day with a level of 1499.7±77.5 pg/ml and 1354.1±105.2 pg/ml, respectively (FIG. 5), and this level of serum INF-γ remained high until the $14^{th}$ day before they returned to a low level as that of the control animals. As to the serum level of IL-2, IL-4, IL-5 and TNF-α, they remained unchanged with or without the vaccination (data not shown). Therefore, this result demonstrates that the combined treatment of poly-rBCG and mIL-12 succeeded in induction of cellular cytokine INF-γ capable of attenuating the growth of cancer cells, and this action is exerting through a cellular (Th1) type response, rather than a humoral (Th2) response within MBT-2 implants.

Example 5

In Vivo Tumor Inhibition by DNA Vaccines

Figure 6:
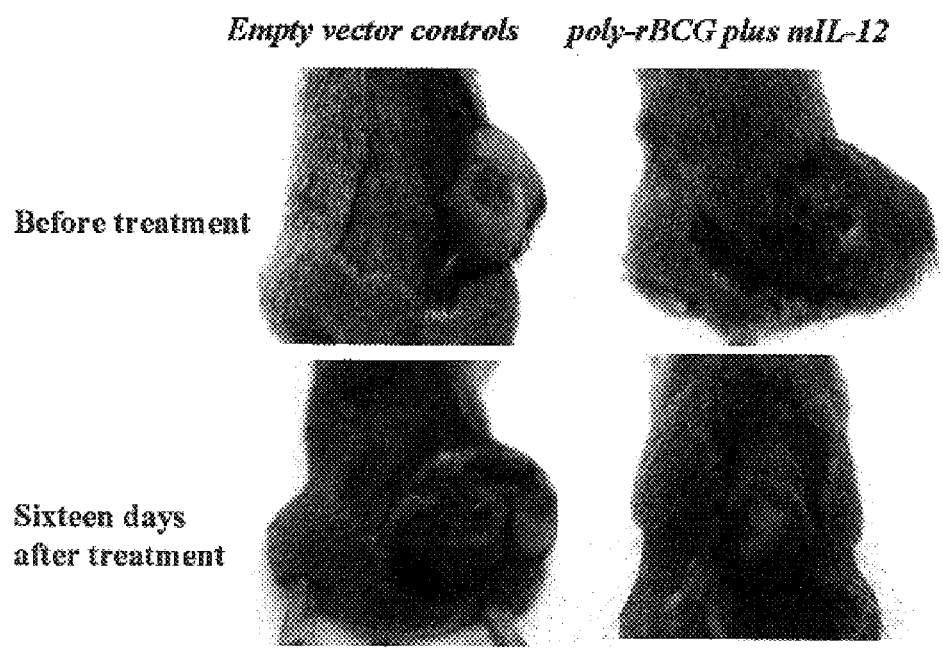
FIG. 6 illustrates the inhibition of tumor growth by combination of poly-rBCG and mIL-12 DNA vaccines of this invention.

Similarly, $C_3H$/HeN mice were first transplanted with MTB-2 tumor according to the procedure described in Example 2, and were then immunized via EPGIT with poly-rBCG vaccine, mIL-12 vaccine, poly-rBCG+mIL-12 vaccines or empty vector (i.e., pCMV-V5-His6 as the control group). Tumor growth was monitored after gene therapy by caliper measurement of tumor volume. Volume was calculated according to the formula, volume=0.52×largest diameter×smallest diameter×thickness. The cumulative survival rate of the mice was periodically determined during 3 months of observation. The results for the inhibition of the growth of implanted tumor and the cumulative survival rate of the mice were shown in FIGS. 6 and 7, respectively.

Figure 7A:
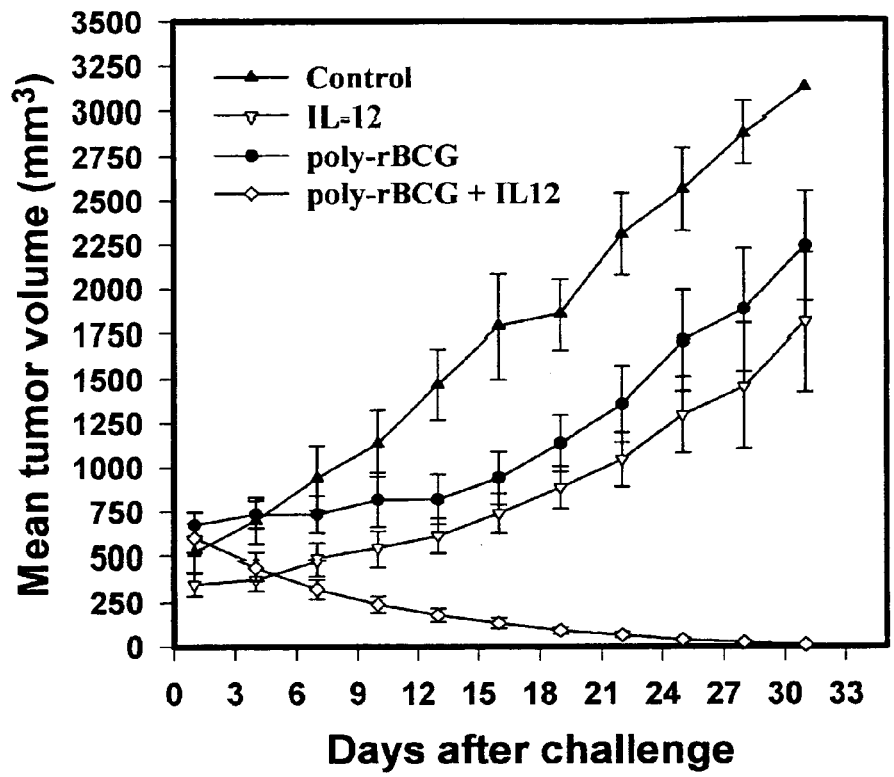
FIG. 7 illustrates the time relationship of mean tumor volume (FIG. 7A) and survival rate of the MBT-2 bearing mice (FIG. 7B) after inoculation with DNA cancer vaccines of this invention, respectively.
Figure 7B:
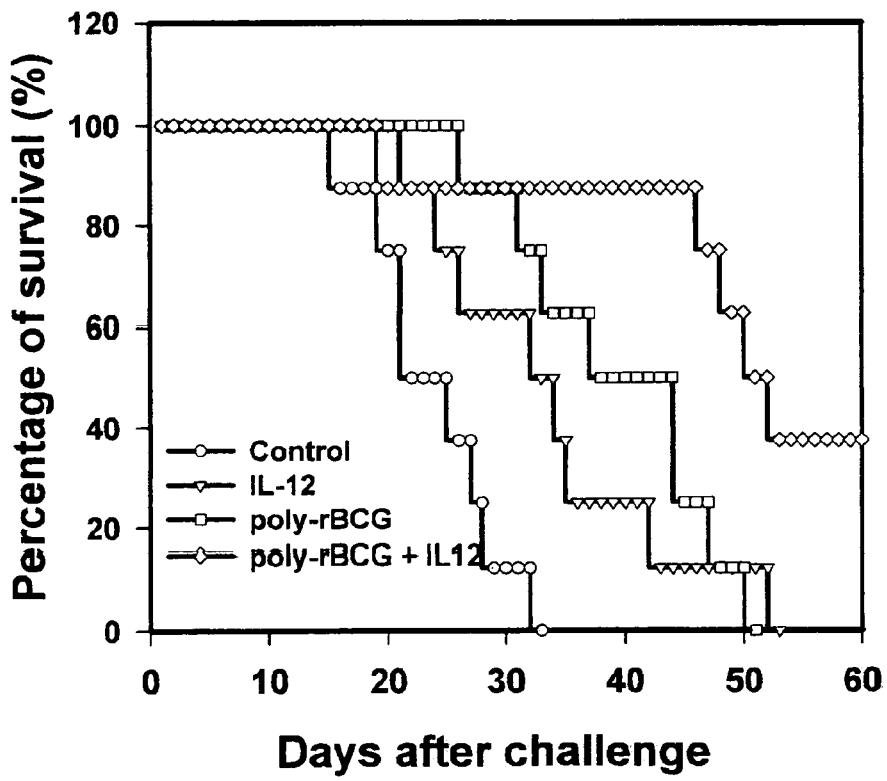

Tumor regression was observed within 16 days in mice that received combined vaccination of poly-rBCG and mIL-12 (FIG. 6), as compared with that of the control animal. At 28 days after electroporation vaccine treatment, the mean volume of MBT-2 implants treated with poly-rBCG or mIL-12 increased 279.90% and 412.78%, respectively (FIG. 7A). Importantly, mean tumor volumes in mice treated with both poly-rBCG and mIL-12 were reduced significantly by 4.08%, demonstrating almost complete tumor regression. All treatments (including poly-rBCG, mIL-12, and poly-rBCG+mIL-12) increased the survival rate of mice (n=8, p<0.5; FIG. 7B), as compared with that of the control animal. However, survival of mice treated with poly-rBCG+mIL-12 was substantially increased within 90-day observation period, when compared with the survival of the other three treatment groups (i.e., vector, poly-rBCG, and mIL-12, respectively). At the time when no mice survived in the mIL-12 group and poly-rBCG group (i.e., day 50), 40% of mice in the poly-rBCG+mIL-12 group were still alive (FIG. 7B). The cumulative survival of mice treated with poly-rBCG+mIL-12 was dramatically higher than for the other three treatment groups around day 45 after treatment. All mice treated with vector alone, mIL-12 alone or poly-rBCG alone died before the end of this experiment. In sum, results of this example demonstrate that DNA cancer vaccine prepared according to the method of this invention, either alone or in combination, may inhibit the growth of a tumor and thereby extending the life span of the treated animals.

The foregoing description of various embodiments of the invention has been presented for purpose of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A DNA cancer vaccine comprising a plasmid vector comprising:
   a) a polynucleotide sequence encoding at least two mycobacterial antigens operably linked to transcription regulatory elements, wherein the two mycobacterial antigens are recombinant BCG antigens of ESAT6; and
   b) an antigen selected from the group consisting of 85A, 85B, Mpt64, and PstS3, and;
   c) an additional polynucleotide sequence encoding an Immunoglobulin kappa (IgK) chain leader sequence that is operably linked to said polynucleotide sequence encoding at least two mycobacterial antigens;
   wherein upon administration to a mammal, said DNA cancer vaccine can effectively attenuate or suppress the growth of bladder cancer cells.

2. The DNA vaccine of claim 1, wherein said mycobacterial antigens are recombinant BOG antigens 85A and ESAT6.

3. The DNA vaccine of claim 1, wherein said mycobacterial antigens are recombinant BOG antigens 85B and ESAT6.

4. The DNA vaccine of claim 1, wherein said mycobacterial antigens are recombinant BOG antigens Mpt64 and ESAT6.

5. The DNA vaccine of claim 1, wherein said mycobacterial antigens are recombinant BOG antigens PstS3 and ESAT6.

6. A composition for attenuating or suppressing the growth of bladder cancer cells comprising: a DNA cancer vaccine, wherein said DNA cancer vaccine comprises:
   a) a first plasmid vector comprising a nucleotide sequence encoding at least two mycobacterial antigens, which are recombinant BCG antigens of ESAT6; and
   b) an antigen selected from the group consisting of 85A, 85B, Mpt64, and PstS3; and
   c) an additional nucleotide sequence encodes Immunoglobulin kappa (IgK) chain leader sequence that is operably linked to said nucleotide sequence encoding at least two mycobacterial antigens;
   and wherein upon administration to a mammal, said composition can effectively attenuate or suppress the growth of bladder cancer cells.

7. The composition of claim 6, wherein said mycobacterial antigens are recombinant BOG antigens 85A and ESAT6.

8. The composition of claim 6, wherein said mycobacterial antigens are recombinant BOG antigens 85B and ESAT6.

9. The composition of claim 6, wherein said mycobacterial antigens are recombinant BOG antigens Mpt64 and ESAT6.

10. The composition of claim 6, wherein said mycobacterial antigens are recombinant BOG antigens PstS3 and ESAT6.

11. The composition of claim 6, further comprising a DNA cancer vaccine comprising a second plasmid vector comprising a polynucleotide sequence encoding a heterodimeric protein of Interleukin-12.

12. The composition of claim 11, wherein the subunits of said heterodimeric protein of Interleukin-12 are mIL-12 p35 and mIL-12 p40.

13. The composition of claim 6, further comprising a chemotherapy agent selected from the group consisting of cisplatin, 5-fluorouracil, vinblastine and adriamycin.

14. The composition of claim 11, further comprising a chemotherapy agent selected from the group consisting of cisplatin, 5-fluorouracil, vinblastine and adriamycin.

* * * * *

```
SEQUENCE LISTING

<160> NUMBER OF SEQ ID NOS: 16

<210> SEQ ID NO 1
<211> LENGTH: 24
<212> TYPE: DNA
<213> ORGANISM: artificial sequence
<220> FEATURE:
<223> OTHER INFORMATION: primer sequence for sense strand of gene Ag85A

<400> SEQUENCE: 1
gtcgactttt cccggccggg cttg                                          24

<210> SEQ ID NO 2
<211> LENGTH: 25
<212> TYPE: DNA
<213> ORGANISM: artificial sequence
<220> FEATURE:
<223> OTHER INFORMATION: primer sequence for antisense strand of gene
      Ag85A

<400> SEQUENCE: 2
gctagcgtct gttcggagcg aggcg                                         25

<210> SEQ ID NO 3
<211> LENGTH: 24
<212> TYPE: DNA
<213> ORGANISM: artificial sequence
<220> FEATURE:
<223> OTHER INFORMATION: primer sequence for sense strand of gene
      Ag85B

<400> SEQUENCE: 3
gtcgacttct cccggccggg gctg                                          24

<210> SEQ ID NO 4
<211> LENGTH: 25
<212> TYPE: DNA
<213> ORGANISM: artificial sequence
<220> FEATURE:
<223> OTHER INFORMATION: primer sequence for antisense strand of gene
      Ag85B
```

```
<400> SEQUENCE: 4
gctagcgccg gcgcctaacg aactc                                              25

<210> SEQ ID NO 5
<211> LENGTH: 28
<212> TYPE: DNA
<213> ORGANISM: artificial sequence
<220> FEATURE:
<223> OTHER INFORMATION: primer sequence for sense strand of gene
      Mpt64

<400> SEQUENCE: 5
cgcggtcgac gcgcccaaga cctactgc                                           28

<210> SEQ ID NO 6
<211> LENGTH: 29
<212> TYPE: DNA
<213> ORGANISM: artificial sequence
<220> FEATURE:
<223> OTHER INFORMATION: primer sequence for antisense strand of gene
      Mpt64

<400> SEQUENCE: 6
ccgggctagc ggccagcatc gagtcgatc                                          29

<210> SEQ ID NO 7
<211> LENGTH: 31
<212> TYPE: DNA
<213> ORGANISM: artificial sequence
<220> FEATURE:
<223> OTHER INFORMATION: primer sequence for sense strand of gene
      PstS3

<400> SEQUENCE: 7
ccgtctcgag tgtggtaacg acgacaatgt g                                       31

<210> SEQ ID NO 8
<211> LENGTH: 28
<212> TYPE: DNA
<213> ORGANISM: artificial sequence
<220> FEATURE:
<223> OTHER INFORMATION: primer sequence for antisense strand of gene
      PstS3

<400> SEQUENCE: 8
gcgggctagc ggcgatcgcg ttgaccgc                                           28

<210> SEQ ID NO 9
<211> LENGTH: 28
<212> TYPE: DNA
<213> ORGANISM: artificial sequence
<220> FEATURE:
<223> OTHER INFORMATION: primer sequence for sense strand of gene
      ESAT6

<400> SEQUENCE: 9
cggcgctagc atgacagagc agcagtgg                                           28

<210> SEQ ID NO 10
<211> LENGTH: 27
<212> TYPE: DNA
<213> ORGANISM: artificial sequence
<220> FEATURE:
<223> OTHER INFORMATION: primer sequence for antisense strand of gene
      ESAT6
```

```
<400> SEQUENCE: 10
ccatcgattg cgaacatccc agtgacg                                          27

<210> SEQ ID NO 11
<211> LENGTH: 26
<212> TYPE: DNA
<213> ORGANISM: artificial sequence
<220> FEATURE:
<223> OTHER INFORMATION: primer sequence for sense strand of gene Ig
      kappa

<400> SEQUENCE: 11
cacaccatgg attttcaagt gcagat                                           26

<210> SEQ ID NO 12
<211> LENGTH: 45
<212> TYPE: DNA
<213> ORGANISM: artificial sequence
<220> FEATURE:
<223> OTHER INFORMATION: primer sequence for antisense strand of gene Ig
      kappa

<400> SEQUENCE: 12
gctagcctag tgccatggtg tcgactcctc tggacattat gactg                      45

<210> SEQ ID NO 13
<211> LENGTH: 30
<212> TYPE: DNA
<213> ORGANISM: artificial sequence
<220> FEATURE:
<223> OTHER INFORMATION: primer sequence for sense strand of gene MlL-1
      2-p35

<400> SEQUENCE: 13
tctagagcta gcatgtgtca atcacgctac                                       30

<210> SEQ ID NO 14
<211> LENGTH: 24
<212> TYPE: DNA
<213> ORGANISM: artificial sequence
<220> FEATURE:
<223> OTHER INFORMATION: Primer sequence for antisense strand of gene
      mlL-1 2-p35

<400> SEQUENCE: 14
gtcgacggcg gagctcagat agcc                                             24

<210> SEQ ID NO 15
<211> LENGTH: 30
<212> TYPE: DNA
<213> ORGANISM: artificial sequence
<220> FEATURE:
<223> OTHER INFORMATION: primer sequence for sense strand of gene MlL-1
      2-p40

<400> SEQUENCE: 15
gctagcgcta gcatgtgtcc tcagaagcta                                       30

<210> SEQ ID NO 16
<211> LENGTH: 24
<212> TYPE: DNA
<213> ORGANISM: artificial sequence
<220> FEATURE:
<223> OTHER INFORMATION: primer sequence for antisense strand of gene
      mlL-1 2-p40
```

```
<400> SEQUENCE: 16
ctcgagggat cggaccctgc aggg                                                              24
```